United States Patent
Tajkef et al.

(10) Patent No.: US 11,358,000 B2
(45) Date of Patent: Jun. 14, 2022

(54) PINEAL GLAND STIMULATOR AND REGULATOR

(71) Applicants: Jack Tajkef, Encino, CA (US); Aaron Massachi, Calabasas, CA (US); Josh Stein, Encino, CA (US); Cody Rudman, Tarzana, CA (US); Harrison Bressler, Encino, CA (US); Ben Robitshek, Woodland Hills, CA (US); Maximillian Winter, Encino, CA (US)

(72) Inventors: Jack Tajkef, Encino, CA (US); Aaron Massachi, Calabasas, CA (US); Josh Stein, Encino, CA (US); Cody Rudman, Tarzana, CA (US); Harrison Bressler, Encino, CA (US); Ben Robitshek, Woodland Hills, CA (US); Maximillian Winter, Encino, CA (US)

( * ) Notice: Subject to any disclaimer, the term of this patent is extended or adjusted under 35 U.S.C. 154(b) by 42 days.

(21) Appl. No.: 16/746,207

(22) Filed: Jan. 17, 2020

(65) Prior Publication Data

US 2020/0230434 A1    Jul. 23, 2020

Related U.S. Application Data

(60) Provisional application No. 62/793,615, filed on Jan. 17, 2019.

(51) Int. Cl.
*A61N 5/06* (2006.01)

(52) U.S. Cl.
CPC .... *A61N 5/0622* (2013.01); *A61N 2005/0626* (2013.01); *A61N 2005/0648* (2013.01);
(Continued)

(58) Field of Classification Search
CPC .......... A61N 5/0622; A61N 2005/0648; A61N 2005/0626; A61N 2005/0651; A61N 2005/0662; A61N 2005/0647
See application file for complete search history.

(56) References Cited

U.S. PATENT DOCUMENTS

| | | | | |
|---|---|---|---|---|
| 5,503,637 A * | 4/1996 | Kyricos | ................ | A61M 21/00 600/27 |
| 6,350,275 B1 * | 2/2002 | Vreman | ................ | A61M 21/00 607/88 |

(Continued)

FOREIGN PATENT DOCUMENTS

| | | | | |
|---|---|---|---|---|
| WO | WO-2014128193 A1 * | 8/2014 | ............ | H05B 45/10 |
| WO | WO-2017013051 A1 * | 1/2017 | ........... | A61N 5/0618 |

OTHER PUBLICATIONS

"Solid State Lighting & Energy Electronics Center, Phospors: Turning Blue Light White, Dec. 15, 2017, UC Santa Barbara Engineering, https://engineering.ucsb.edu/news/phosphors-turning-blue-light-white" (Year: 2017).*

(Continued)

*Primary Examiner* — Joseph M Dietrich
*Assistant Examiner* — Michael T. Holtzclaw
(74) *Attorney, Agent, or Firm* — Alston & Bird LLP (57) ABSTRACT

An apparatus is provided for ocular stimulation. In embodiments, the apparatus comprises ocular stimulator circuitry couplable with a headwear item, and a plurality of ocular stimulator LED packages electrically couplable to the ocular stimulator circuitry. The plurality of ocular stimulator LED packages are configured to stimulate a pineal gland associated with a live subject on which the headwear item is disposed. The apparatus may be configured to cause the ocular stimulator LED packages to emit light according to at least one pre-programmed operating mode.

26 Claims, 8 Drawing Sheets

(52) U.S. Cl.
CPC .............. *A61N 2005/0651* (2013.01); *A61N 2005/0662* (2013.01)

(56) References Cited

U.S. PATENT DOCUMENTS

| | | | | |
|---|---|---|---|---|
| 8,721,698 | B2* | 5/2014 | Pederson | A61M 21/00 607/90 |
| 2005/0237479 | A1* | 10/2005 | Rose | G02B 27/017 351/123 |
| 2005/0278003 | A1* | 12/2005 | Feldman | A61N 5/0618 607/88 |
| 2010/0179469 | A1* | 7/2010 | Hammond | A61N 5/0624 604/20 |
| 2012/0245660 | A1* | 9/2012 | Pederson | A61M 21/00 607/90 |
| 2013/0178920 | A1 | 7/2013 | Givertz et al. | |
| 2016/0158485 | A1* | 6/2016 | Givertz | A61N 5/0618 607/90 |
| 2016/0158486 | A1* | 6/2016 | Colbaugh | A61N 5/0618 607/88 |
| 2018/0074322 | A1* | 3/2018 | Rousseau | G02B 27/017 |

OTHER PUBLICATIONS

ARDUINO®, https://www.arduino.cc/, accessed on Apr. 7, 2020, website available as early as Jan. 18, 2006 per Internet Archive Wayback Machine, 9 pages.

Ledinside, Research Finds Blue Light Exposure Helps to Decrease Blood Pressure, Nov. 19, 2018, retrieved from https://m.ledinside.com/node/view/29878.html on Apr. 7, 2020.

Resmed, S+: Darkness Matters—How Light Affects Sleep, Copyright 2015, retrieved from http://sleep.mysplus.com/library/category2/article1.html on Apr. 7, 2020.

* cited by examiner

PINEAL GLAND STIMULATOR AND REGULATOR

CROSS-REFERENCE TO RELATED APPLICATIONS

The present application claims priority to and the benefit of U.S. Provisional Application Ser. No. 62/793,615, titled "PERSONAL PINEAL GLAND LIGHT STIMULATOR AND REGULATOR," filed Jan. 17, 2019; the contents of which as are hereby incorporated herein by reference in their entirety.

BACKGROUND

Light emitting devices may comprise light emitting diodes. Light emitting diodes (also referred to herein as LEDs) are semiconductor devices that emit light when an electric current is passed through them. The light is produced when particles that carry the electric current (i.e., electrons and holes) combine together with the semiconductor material of the semiconductor devices. LEDs are described as solid-state devices, which distinguishes them from other lighting technologies that use heated filaments or gas discharge as lighting sources (e.g., incandescent, tungsten halogen lamps; fluorescent lamps).

LEDs are widely used in myriad applications. For example, LEDs may be utilized as light sources in light therapy applications. Specifically, LEDs may simulate natural light cycles of an individual.

However, conventional personal light therapy devices are deficient as far as portability, power, inconspicuousness of design, and safety. There is lacking a solution for personal ocular stimulation that is portable, discreet, powerful, and all the while safe.

Through applied effort, ingenuity, and innovation many deficiencies of conventional systems have been solved by developing solutions that are in accordance with the embodiments of the present invention, many examples of which are described in detail herein.

SUMMARY

Various embodiments are directed to an LED apparatus for ocular stimulation. In certain embodiments, the apparatus comprises ocular stimulator circuitry couplable with a headwear item. In certain embodiments, a plurality of ocular stimulator LED packages are electrically couplable to the ocular stimulator circuitry. In embodiments, the plurality of ocular stimulator LED packages are configured to stimulate a pineal gland associated with a live subject on which the headwear item may be disposed.

In certain further embodiments, the plurality of ocular stimulator LED packages are positioned in front of an ocular orbit of the live subject.

The plurality of ocular stimulator LED packages of certain embodiments are configured to stimulate the pineal gland by mimicking a level of light associated with one or more times of day.

In embodiments, a level of light is one or more of sunrise low-level light associated with an actual or virtual sunrise, daytime full intensity light associated with an actual or virtual day, or sunset low-level light associated with an actual or virtual sunset.

In certain embodiments, the ocular stimulator circuitry comprises a circuit board having a first circuit board side and a second circuit board side. In certain embodiments, the plurality of ocular stimulator LED packages is one or more of disposed on or electrically and mechanically couplable with the first circuit board side.

In certain embodiments, a plurality of leads/traces is one or more of disposed on or electrically and mechanically couplable with the first circuit board side or the second circuit board side and electrically couplable with the plurality of ocular stimulator LED packages. In certain embodiments, driver circuitry is disposed on and/or electrically and mechanically couplable with the first circuit board side or the second circuit board side. The driver circuitry of certain embodiments is electrically couplable with the plurality of leads/traces of the circuit board.

In certain embodiments, the driver circuitry is configured to control one or more of positions of the plurality of ocular stimulator LED packages, intensities of the plurality of ocular stimulator LED packages, or a schedule associated with light levels provided by the plurality of ocular stimulator LED packages.

The driver circuitry of certain embodiments is configured to detect the ocular orbit associated with the live subject and adjust one or more positions of the plurality of ocular stimulator LED packages according to the ocular orbit.

In embodiments, the apparatus further comprises a power source electrically couplable with the ocular stimulator circuitry.

In embodiments, the plurality of ocular stimulator LED packages are configured to emit white light.

In embodiments, the plurality of ocular stimulator LED packages comprise one or more of red, green and blue LEDs.

In certain embodiments, the plurality of ocular stimulator LED packages comprise phosphor-based blue LEDs.

The phosphor-based blue LEDs of certain embodiments are configured to provide a range of color temperatures from 2400K to 5000K.

In embodiments, the apparatus further comprises ocular stimulator attachment means.

The ocular stimulator attachment means of certain embodiments is configured to attach the apparatus to an article of headwear.

In certain embodiments, the driver circuitry is configured to cause the ocular stimulator LED packages to emit light according to at least one pre-programmed operating mode.

In certain embodiments, the apparatus further comprises wireless communication means for communication with one or more client devices.

The apparatus of certain embodiments is configured to receive instructions from the one or more client devices.

In certain embodiments, the instructions modify one or more of positions of the plurality of ocular stimulator LED packages, intensities of the plurality of ocular stimulator LED packages, or a schedule associated with light levels provided by the plurality of ocular stimulator LED packages.

This Summary does not attempt to completely signify any particular innovation, embodiment, or example as it can be used in commerce. Additionally, this Summary is not intended to signify essential elements of an innovation, embodiment or example or to limit the scope of the subject matter of this disclosure.

The innovations, embodiments, and/or examples found within this disclosure are not all-inclusive, but rather describe the basic significance of the subject matter. Accordingly, one use of this Summary is as a prelude to a Detailed Description presented later.

BRIEF DESCRIPTION OF THE DRAWINGS

The following Detailed Description, Figures, and appended Claims signify the nature and advantages of the innovations, embodiments and/or examples of the claimed inventions. All of the Figures signify innovations, embodiments, and/or examples of the claimed inventions for purposes of illustration only and do not limit the scope of the claimed inventions. Such Figures are not necessarily drawn to scale, and are part of the Disclosure.

In the Figures, similar components or features may have the same, or similar, reference signs in the form of labels (such as alphanumeric symbols, e.g., reference numerals), and may signify similar or equivalent functionality. Further, various components of the same type may be distinguished by following the reference label by a dash and a second label that distinguishes among the similar components. If only the first reference label is used in the specification, the description is applicable to any one of the similar components having the same first reference label irrespective of the second reference label. A brief description of the Figures is below.

DETAILED DESCRIPTION

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

It is an objective of the present disclosure to provide a personal apparatus for ocular stimulation of the pineal gland having improved portability, discretion, and safety over conventional systems.

Conventional systems do not provide portability while simultaneously providing sufficient light output and safety. Conventional systems are either bulky, and difficult to move, or conventional systems are portable but yet indiscreet and lacking power. It is therefore an objective of the present disclosure to provide an apparatus for ocular stimulation that is configured to be discreet, safe and of sufficient intensity. Thus, the apparatus of the present disclosure employs LEDs to provide light of suitable wavelength and spectral power distribution to achieve ocular stimulation of the pineal gland.

The present disclosure provides ocular stimulator circuitry that may be coupled with a headwear item so as to be portable and discreet. The headwear item may be specifically designed or modified for this purpose, or it may be a headwear item of personal, everyday use. For example, the headwear item may be a visor, hat, helmet, or the like. The apparatus of the present disclosure may be coupled to any part of the headwear item for convenience. Particularly, the ocular stimulator circuitry may be coupled on either the top or underside of the brim of a headwear item. The LEDs employed by the apparatus of the present disclosure may be positioned in front of the ocular orbit of an individual.

It is another objective of the present disclosure to provide improved functionality over conventional systems. The light output of the LEDs employed by an apparatus according to the present disclosure may therefore be programmed and controlled by an individual. To achieve this functionality, an apparatus for ocular stimulation according to the present disclosure may be configured to communicate with one or more wired and/or wireless devices. Hence, user functionality and preferences may be communicated with regard to the light cycle and light output of an apparatus for ocular stimulation according to the present disclosure. A more detailed description will now be made with reference to the accompanying figures.

Figure 1A:
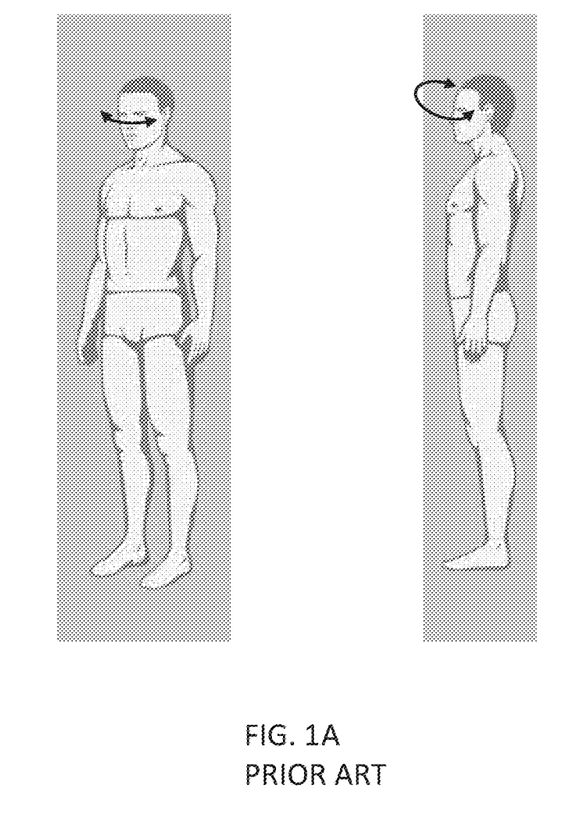
FIG. 1A is a perspective view indicating an exemplary range around the human eyes that is useful for an apparatus for ocular stimulation according to various embodiments.
Figure 1B:
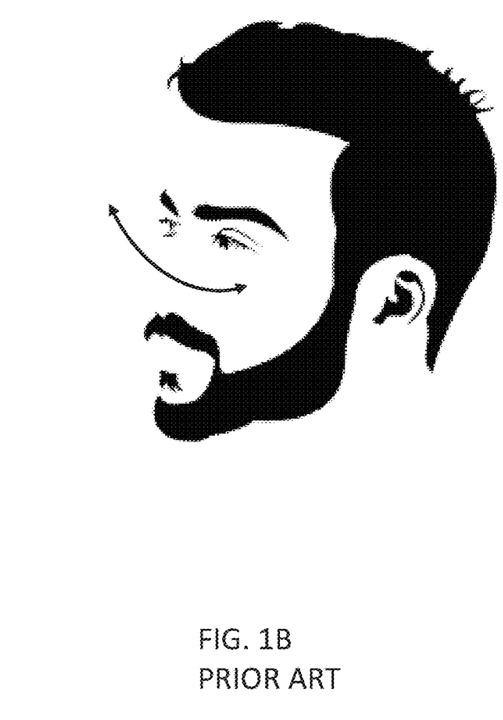
FIG. 1B is a perspective view indicating an exemplary range around the human eyes that is useful for an apparatus for ocular stimulation according to various embodiments.

FIGS. 1A-1B illustrate an exemplary range around the human eyes that is useful for an apparatus for ocular stimulation according to various embodiments. The ocular orbit is the cavity or socket of the skull in which the eye and its appendages are situated. The pineal gland is a small endocrine gland within the brain of most vertebrates. Light stimulation of the eye via the ocular orbit can influence the synthesis and release of chemicals by the pineal gland.

Figure 2A:
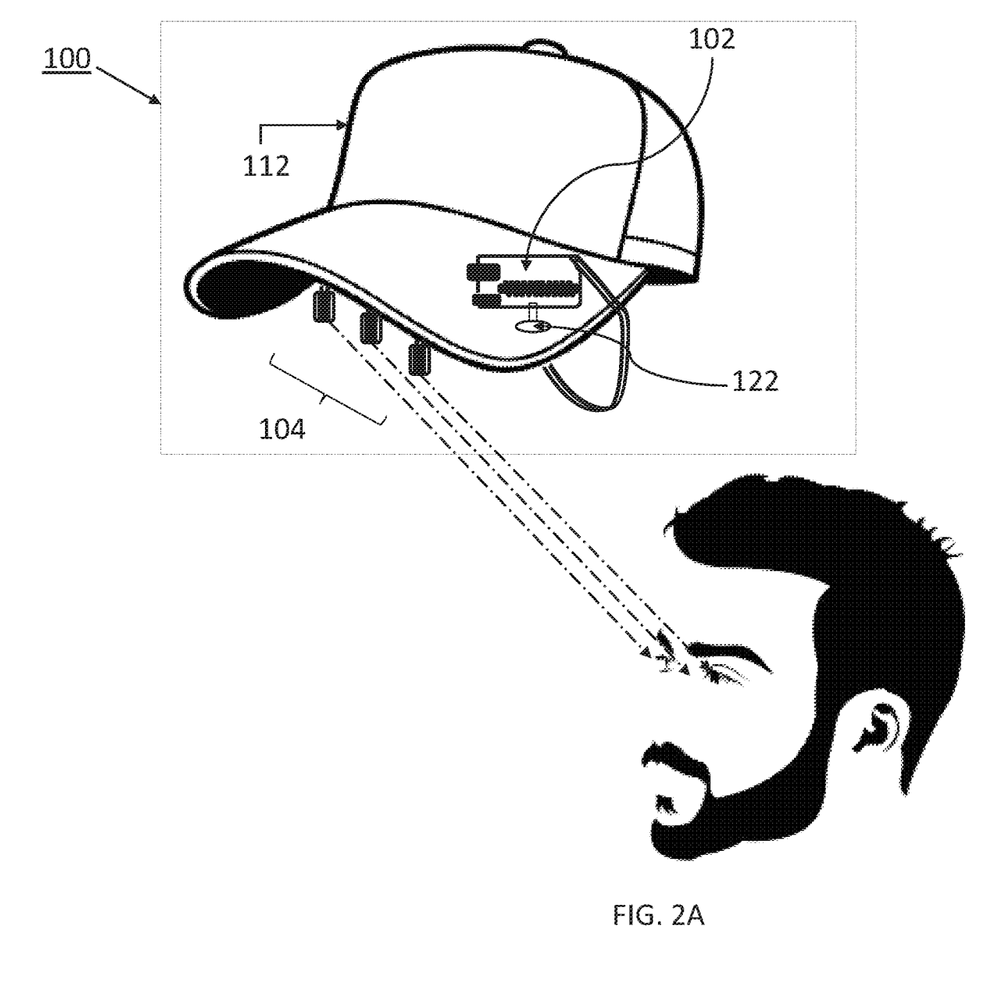
FIG. 2A is a perspective view of an exemplary apparatus for ocular stimulation according to various embodiments.

FIG. 2A illustrates an exemplary apparatus for ocular stimulation 100 configured in accordance with embodiments of the present disclosure. In embodiments, an apparatus for ocular stimulation 100 may comprise ocular stimulator circuitry 102. The ocular stimulator circuitry 102 may be couplable with a headwear item 112. In embodiments, ocular stimulator attachment means 122 (e.g., a sew-on button, a ball-and-socket snap, Velcro, adhesive, or the like) couples the ocular stimulator circuitry 102 to a headwear item 112.

The headwear item 112 may be specially designed for integration with an apparatus for ocular stimulation 100, or may be conventional headwear such as a visor, hat, helmet or any other headwear that is modified by an apparatus for ocular stimulation 100.

An apparatus for ocular stimulation 100 may be configured such that the ocular stimulator circuitry 102 is couplable to any part of a headwear item 112. In embodiments, an apparatus for ocular stimulation 100 may comprise a plurality of ocular stimulator LED packages 104. The plurality of ocular stimulator packages 104 may be electrically couplable to the ocular stimulator circuitry 102, such that the ocular stimulator LED packages 104 may be configured to stimulate a pineal gland associated with a live subject on which the headwear item 112 is disposed.

The apparatus for ocular stimulation 100 may be configured such that the ocular stimulator LED packages 104 are arranged on the underside of the brim of a headwear item 112, in front of the ocular orbit of an individual. The ocular stimulator LED packages 104 may comprise one or more of over molded packaged LEDs or surface mount LED packages.

In embodiments, white light may be the preferred light color to be used. To achieve white light, red, green, and blue LEDs may be used in combination. Blue LEDs using phosphor to convert blue light to white light may be used. Other color LEDs, such as amber and/or red may be used to influence or provide a desired light color. In the case of blue LED phosphor converted white light, the phosphor may be selected to provide a range of color temperature from warm white (for example 2400K) to cool white (5000K). Warm white ocular stimulator LED packages 104 and cool white ocular stimulator LED packages 104 may be employed.

The ocular stimulator LED packages 104 may mimic a level of light associated with one or more times of day. The beginning of a light cycle may start with low intensity warm white light, increasing over time and adding the cool white light at increasing intensity so that by the midday time of the light cycle, both warm white and cool white ocular stimulator LED packages 104 are illuminated at a high intensity. Then as the light cycle progresses, the cool white ocular stimulator LED packages 104 may dim in intensity followed by the warm white ocular stimulator LED packages 104 dimming in intensity. The cool white ocular stimulator LED packages 104 may switch off, and then eventually the warm white ocular stimulator LED packages 104 may switch off. Red or amber LEDs may be added to the programmed light cycle at the beginning and/or at the end of the light cycle.

The LED selection and the LED programming may be made to address the research and desired objective for an artificial light cycle. Light intensity during the day, for a full engagement of activities, may be as high as 100,000 lux. A preferred light intensity may be between 2,500 lux and 10,000 lux during the day, at 2.4 inches away from the ocular orbit of a user. At bedtime, light intensity may drop to as low 180 lux and then may drop further to 5 lux or lower when it is time to sleep.

Figure 2B:
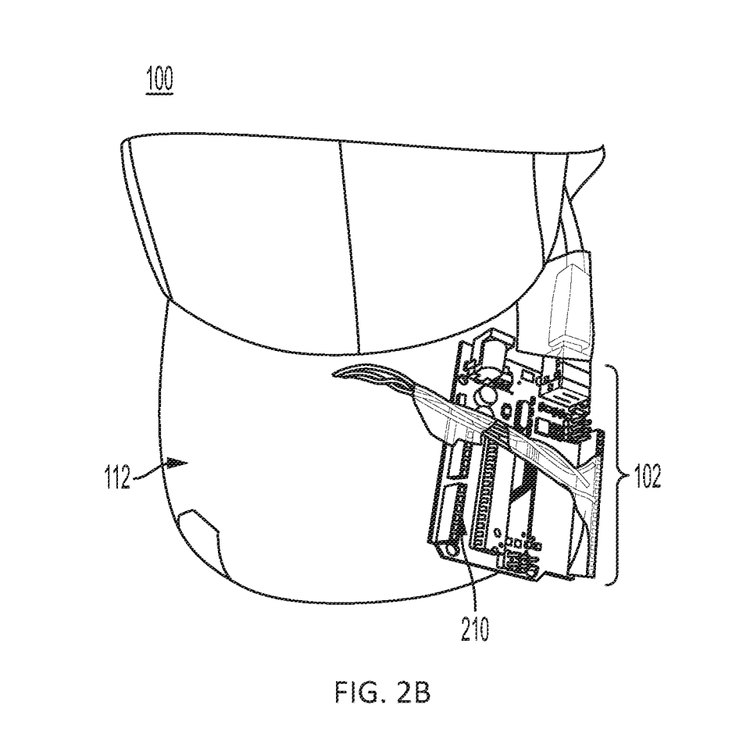
FIG. 2B is a top view of an exemplary apparatus for ocular stimulation according to various embodiments.
Figure 2C:
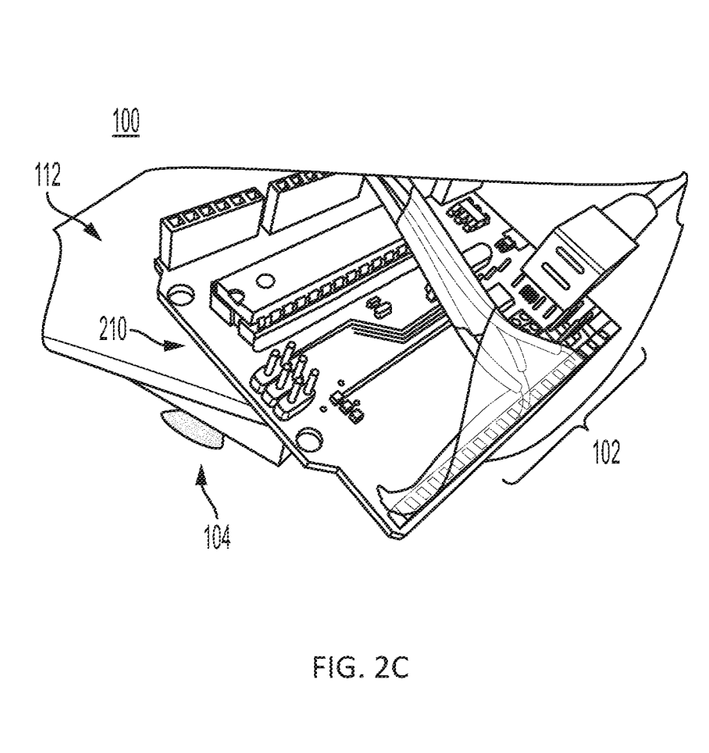
FIG. 2C is a perspective view of an exemplary apparatus for ocular stimulation according to various embodiments.

FIGS. 2A-2C illustrate an exemplary apparatus for ocular stimulation 100 configured in accordance with embodiments of the present disclosure. In embodiments, an exemplary apparatus for ocular stimulation 100 may comprise ocular stimulator circuitry 102, and a plurality of ocular stimulator LED packages 104. The ocular stimulator circuitry 102 may be couplable with a headwear item 112. The headwear item 112 may be specially designed for that purpose or may be modified conventional headwear items 112 such as a visor, hat, helmet, etc. The ocular stimulator LED packages 104 may comprise one or more of over molded packaged LEDs or surface mount LED packages. In embodiments, white light may be the preferred light color to be used. To achieve white light, red, green, and blue LEDs may be used in combination.

Figure 2D:
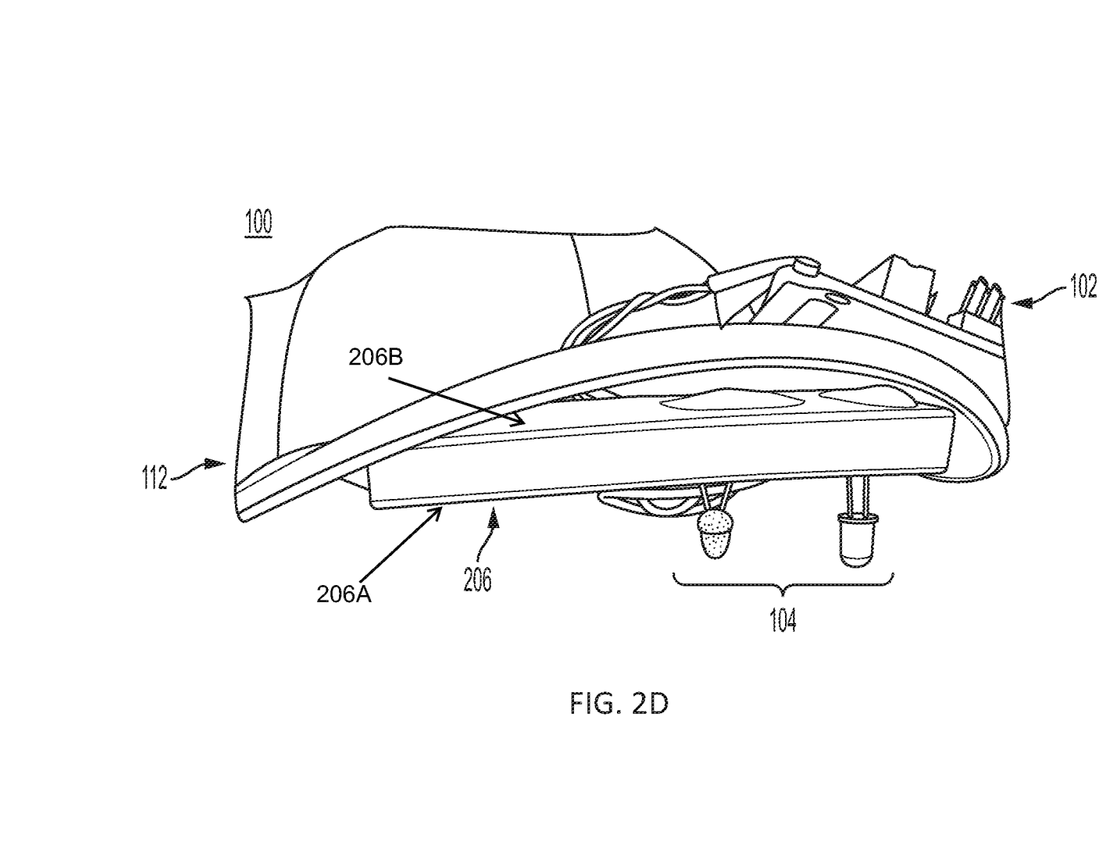
FIG. 2D is a front view of an exemplary apparatus for ocular stimulation according to various embodiments.

As illustrated in FIG. 2D, the ocular stimulator circuitry 102 of an exemplary apparatus for ocular stimulation 100 may further comprise a circuit board 206. It will be appreciated that the ocular stimulator circuitry 102 of an exemplary apparatus for ocular stimulation 200 may alternatively comprise a breadboard. The circuit board 206 of an exemplary apparatus for ocular stimulation 100 may comprise a first circuit board side 206A and a second circuit board side 206B. The plurality of ocular stimulator LED packages 104 of an exemplary apparatus for ocular stimulation 100 may be one or more of disposed on or electrically and mechanically couplable with the first circuit board side 206A. The ocular stimulator LED packages 104 of exemplary embodiments may be mounted on a circuit board 206 or a breadboard on the underside of the brim of a headwear item 112. The ocular stimulator LED packages 104 of exemplary embodiments, particularly if of the discrete over molded type, may be mounted directly to the brim of a headwear item 112.

In exemplary apparatus for ocular stimulation 100, a plurality of leads/traces 108 may be one or more of disposed on or electrically and mechanically couplable with the first circuit board side 206A or the second circuit board side 206B, and electrically couplable to the plurality of ocular stimulator LED packages 104. In exemplary embodiments, driver circuitry 210 may be disposed on and/or electrically and mechanically couplable with the first circuit board side 206A or second circuit board side 206B. The driver circuitry 210 of exemplary embodiments is electrically couplable with the plurality of leads/traces 108 of the circuit board 206.

In embodiments, the driver circuitry 210 may be configured to control one or more of the positions of, intensities of, or a schedule associated with the light levels provided by the plurality of ocular stimulator LED packages 104. In embodiments, the driver circuitry 210 may be configured to detect the ocular orbit associated with the live subject and adjust one or more positions of the plurality of ocular stimulator LED packages 104 according to the ocular orbit.

To detect the ocular orbit of a live subject, the driver circuitry 210 may employ techniques including eye tracking and/or eye and orbit anthropometry. The driver circuitry 210 may employ sensors configured to track the eye movement of the live subject. Hence, driver circuitry 210 may employ one or more sensors to detect the ocular orbit of a live subject. For example, one or more sensors may be configured to estimate geometric data representing the eye position and/or visual point of focus of a live subject. One or more sensors may separately estimate the eye position and/or visual focus point of the left and right eyes of a live subject. One or more sensors may simultaneously estimate geometric data for both eyes. The driver circuitry 210 may be configured to interpret this geometric data estimated by one or more sensors as complementary geometric data representing the ocular orbit associated with a live subject. One or more sensors employed by driver circuitry 210 for detecting the ocular orbit associated with the live subject may be embedded within a headwear item 112 or may be configured as a peripheral device.

A microcontroller 210, for example an Arduino® microcontroller as shown in FIGS. 2B-2D or any other suitable microcontroller 210, may be used to control the ocular stimulator LED packages 104 according to a program for the desired artificial light cycle. Multiple programs may be stored in a memory of the microcontroller 210. Programs may be downloadable by means of a USB connection. Alternatively, programs may be downloaded and/or transmitted wirelessly. Power for the ocular stimulator LED packages 104 may be provided by a battery pack that may also be rechargeable. The battery pack may be couplable with the headwear item 112 (i.e., couplable on the top of the brim of the headwear item 112, about the circumference of the headwear item 112, disposed within the material comprising the headwear item 112, for example when the headwear item 112 is a helmet, or on the back of the headwear item 112). Further, the battery pack may be located elsewhere, for example, on the belt or in a pocket of the user and electrically couplable to the ocular stimulator circuitry 102. The USB connection may also be configured to charge the battery pack.

Figure 3A:
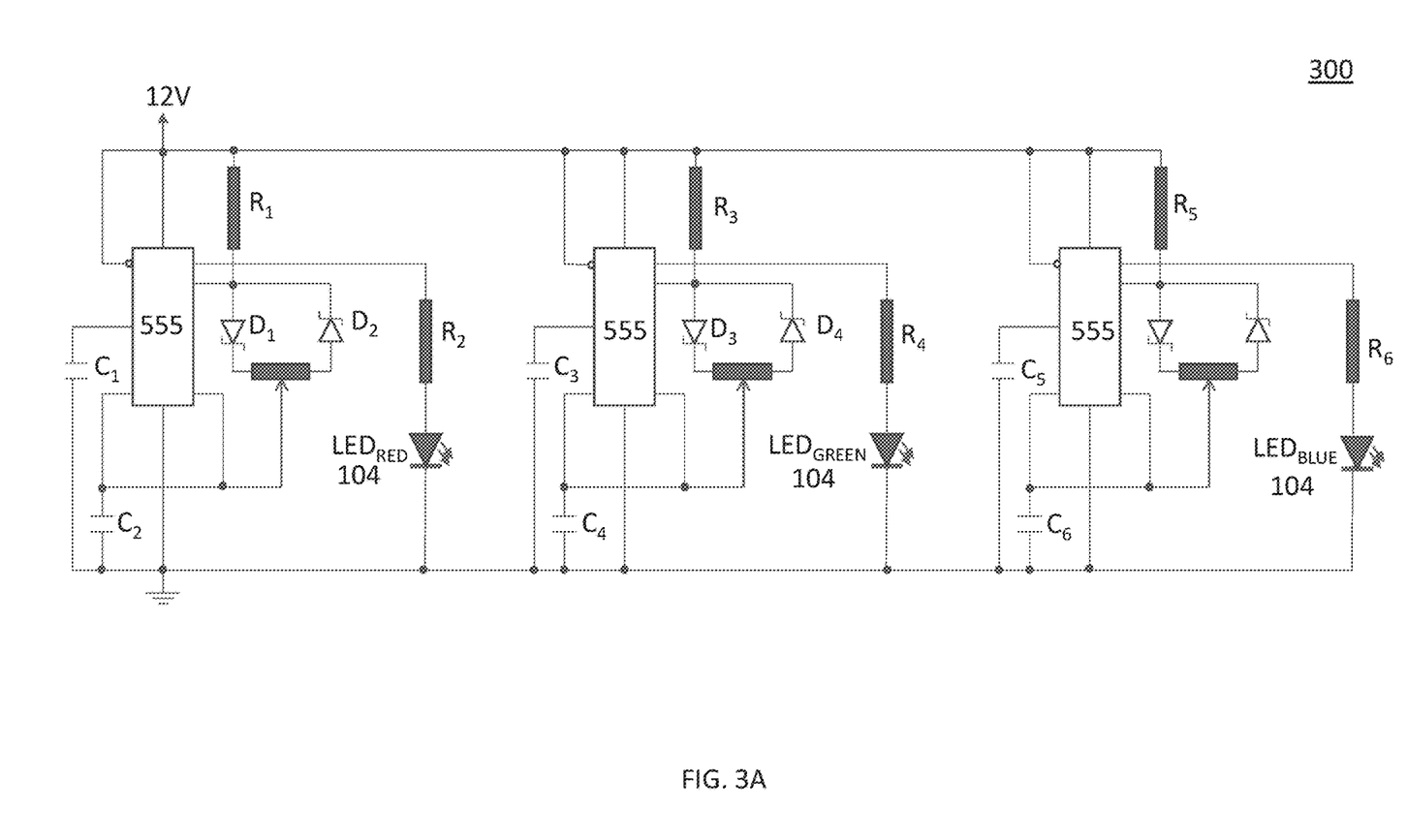
FIG. 3A is a schematic of circuitry employed in an exemplary apparatus for ocular stimulation according to an exemplary embodiment.
Figure 3B:
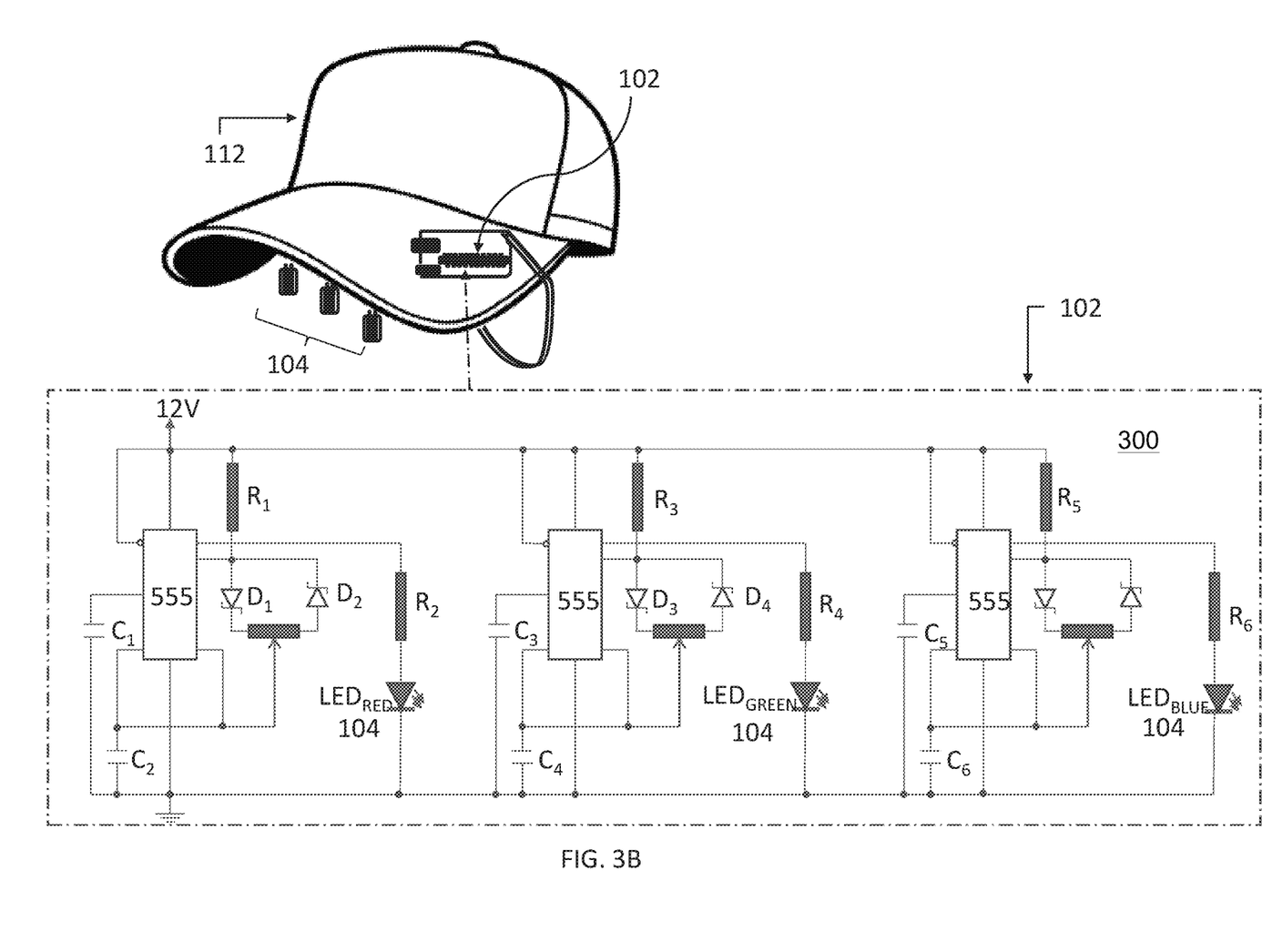
FIG. 3B is a hardware architecture diagram of circuitry employed in an exemplary apparatus for ocular stimulation according to an exemplary embodiment.

FIGS. 3A-3B illustrate circuitry 300 that may be employed in an exemplary apparatus for ocular stimulation 100. FIG. 3A illustrates circuitry 300 configured to achieve white light of varying perceived brightness by employing red, green, and blue ocular stimulator packages 104. The dashed box of FIG. 3B illustrates that the circuitry 300 may be configured within the ocular stimulator circuitry 102. The circuitry 300 may employ red, green and blue ocular stimulation LED packages 104 to achieve white light. Timer ICs may be employed to control the brightness of each red, green, or blue ocular stimulation LED package 104 by implementing Pulse-Width Modulation. Exemplary Timer ICs, such as 555 Timer ICs as shown, may therefore act as astable multivibrators in circuitry 300. Two switching diodes may be utilized in conjunction to help with capacitor charging and discharging. As a result, the circuitry 300, may achieve white light of varying perceived brightness according to a program for the desired artificial light cycle.

Figure 4:
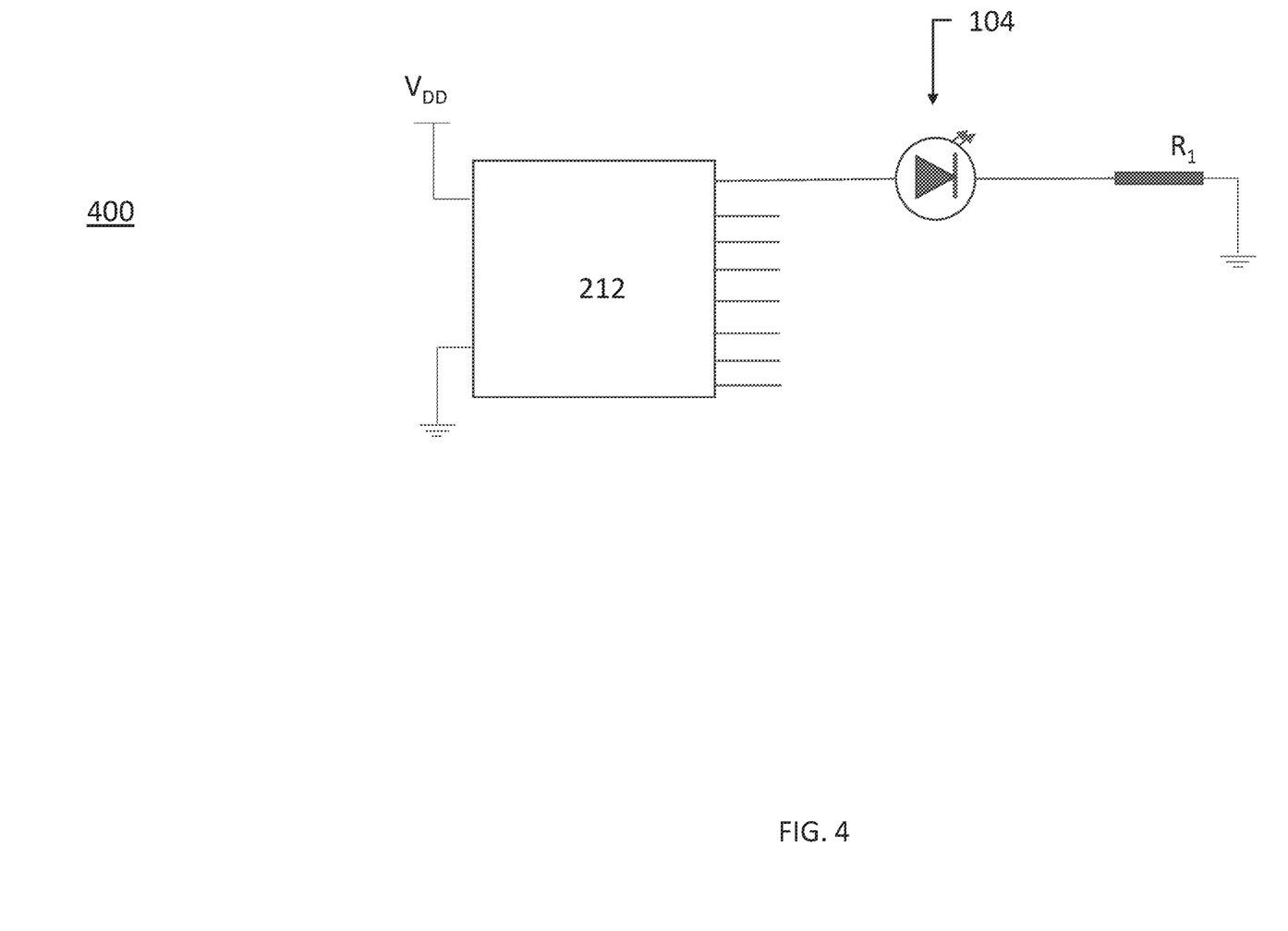
FIG. 4 is a schematic of circuitry employed in an exemplary apparatus for ocular stimulation according to various embodiments.

FIG. 4 illustrates circuitry 400 that may be employed to achieve white light of varying perceived brightness. The circuitry 400 may employ a microcontroller 212 to achieve automatic sequencing and/or control the circuitry. The circuitry 400 may thus employ one or more white ocular stimulation LED packages 104. The microcontroller 212 may be programmable to automatically control and vary the perceived brightness of the white ocular stimulation LED packages 104 according to a program for the desired artificial light cycle. For example, the microcontroller 212 may implement Pulse-Width Modulation to vary the perceived brightness of the white ocular stimulator LED packages 104.

Figure 5:
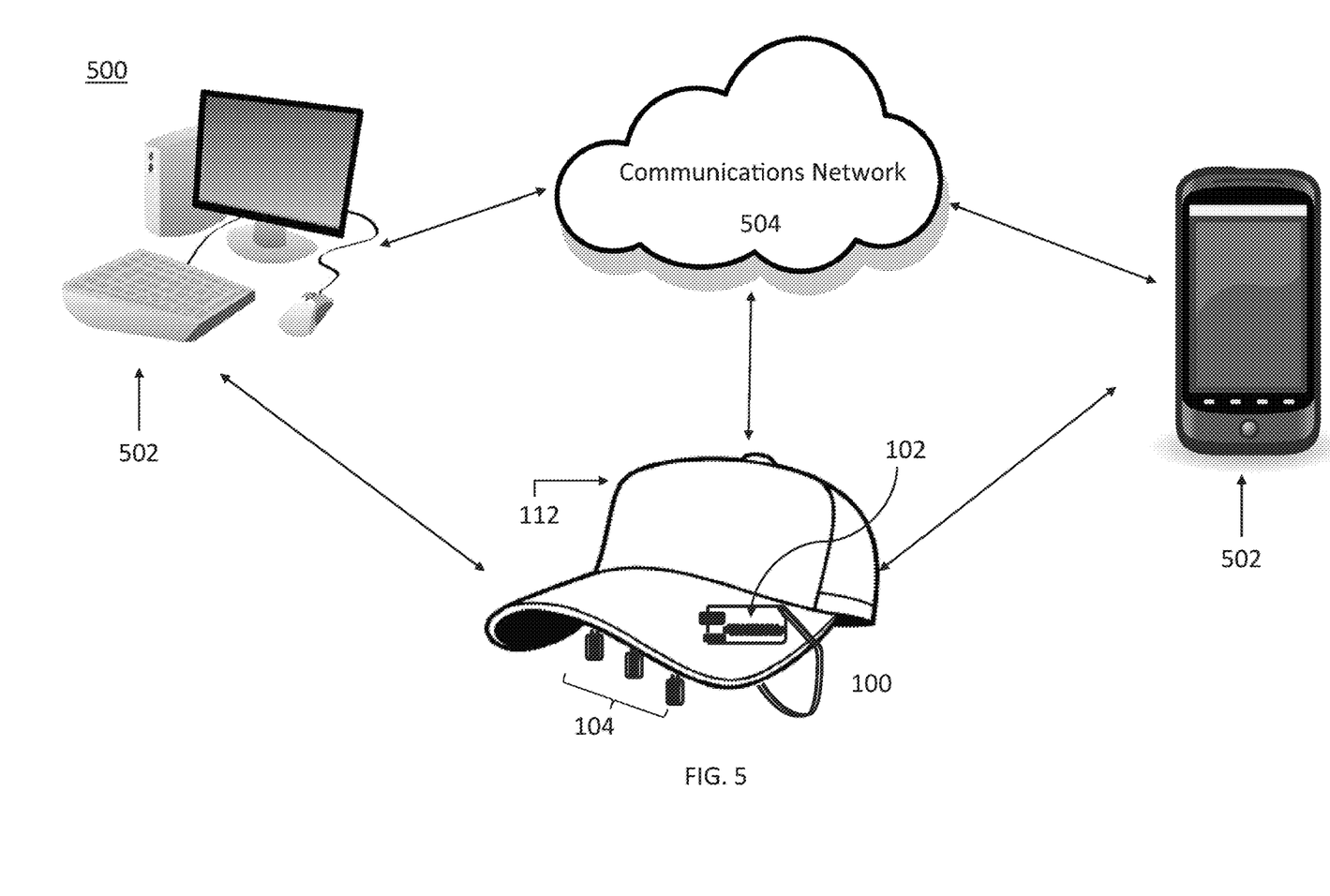
FIG. 5 illustrates a system within which an exemplary apparatus for ocular stimulation may operate according to various embodiments.

FIG. 5 illustrates a system 500 within which an apparatus for ocular stimulation 100 may operate. In embodiments, an apparatus for ocular stimulation 100 may further comprise wireless communication means for communication with one or more client devices 502. Client devices 502 may comprise computing devices such as, mobile phones, smart phones, PDAs, laptops, tablets or the like. Communications network 504 may include any wired or wireless communication network including, for example, a wired or wireless local area network (LAN), personal area network (PAN), metropolitan area network (MAN), wide area network (WAN), or the like. The communications network 504 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Likewise, a wireless client device 502 may communicate with the communications network 504 via multiple wireless communication standards and protocols. The stimulator circuitry 102 may thus further be configured to be electronically couplable with a communications network 504 to achieve wireless communication over the communications network 504.

An apparatus for ocular stimulation 100 may be configured such that the stimulator circuitry 102 accommodates a direct, wired connection to a mobile or non-mobile computing device 502. A direct, wired connection between the circuitry 102 of an apparatus for ocular stimulation and a client device 502 may be achieved in accordance with multiple wired communication standards and protocols, such as fiber distributed data interface (FDDI), digital subscriber line (DSL), Ethernet, asynchronous transfer mode (ATM), frame relay, data over cable service interface specification (DOCSIS), or any other wired transmission protocol.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. An apparatus for ocular stimulation, the apparatus comprising:
   ocular stimulator circuitry couplable with a headwear item; and
   a plurality of ocular stimulator LED packages electrically couplable to the ocular stimulator circuitry, wherein the plurality of ocular stimulator LED packages are configured to stimulate a pineal gland associated with a live subject on which the headwear item is disposed; and
   driver circuitry configured to detect an ocular orbit associated with the live subject and adjust one or more positions of the plurality of ocular stimulator LED packages according to the ocular orbit, wherein the ocular orbit is a cavity or socket of a skull of the live subject in which an eye of the live subject is situated, and wherein detecting the ocular orbit comprises obtaining geometric data representing a visual focus point associated with the left eye and the right eye of the live subject and determining the ocular orbit based at least in part on the visual focus point of the left eye and the right eye of the live subject.

2. The apparatus of claim 1, wherein the plurality of ocular stimulator LED packages are positioned in front of the ocular orbit of the live subject.

3. The apparatus of claim 1, wherein the plurality of ocular stimulator LED packages are configured to stimulate the pineal gland by mimicking a level of light associated with one or more times of day.

4. The apparatus of claim 3, wherein the level of light is one or more of sunrise low-level light associated with an actual or virtual sunrise, daytime full intensity light associated with an actual or virtual day, or sunset low-level light associated with an actual or virtual sunset.

5. The apparatus of claim 1, wherein the ocular stimulator circuitry comprises a circuit board, the circuit board having a first circuit board side and a second circuit board side.

6. The apparatus of claim 5, wherein the plurality of ocular stimulator LED packages is one or both of disposed on or electrically and mechanically couplable with the first circuit board side.

7. The apparatus of claim 6, further comprising wireless communication means for communication with one or more client devices.

8. The apparatus of claim 7, configured to receive instructions from the one or more client devices.

9. The apparatus of claim 8, wherein the instructions modify one or more of positions of the plurality of ocular stimulator LED packages, intensities of the plurality of ocular stimulator LED packages, or a schedule associated with light levels provided by the plurality of ocular stimulator LED packages.

10. The apparatus of claim 5, wherein a plurality of leads/traces is one or both of disposed on or electrically and mechanically couplable with the first circuit board side or the second circuit board side and electrically couplable to the plurality of ocular stimulator LED packages.

11. The apparatus of claim 5, wherein the driver circuitry is disposed on and/or electrically and mechanically couplable with the first circuit board side or second circuit board side, the driver circuitry electrically couplable with the plurality of leads/traces of the circuit board.

12. The apparatus of claim 11, wherein the driver circuitry is configured to control one or more of positions of the plurality of ocular stimulator LED packages, intensities of the plurality of ocular stimulator LED packages, or a schedule associated with light levels provided by the plurality of ocular stimulator LED packages.

13. The apparatus of claim 11, wherein the driver circuitry is configured to cause the ocular stimulator LED packages to emit light according to at least one pre-programmed operating mode.

14. The apparatus of claim 1, further comprising a power source electrically couplable with the ocular stimulator circuitry.

15. The apparatus of claim 1, wherein the plurality of ocular stimulator LED packages are configured to emit white light.

16. The apparatus of claim 15, wherein the plurality of ocular stimulator LED packages comprises one or more of red, green and blue LEDs.

17. The apparatus of claim 16, wherein the plurality of ocular stimulator LED packages comprises phosphor-based blue LEDs.

18. The apparatus of claim 17, wherein the phosphor-based blue LED packages are configured to provide a range of color temperatures from 2400K to 5000K.

19. The apparatus of claim 1, further comprising ocular stimulator attachment means.

20. The apparatus of claim 19, wherein the ocular stimulator attachment means are configured to attach the apparatus to an article of headwear.

21. A method for ocular stimulation, comprising:
  detecting, using ocular stimulator circuitry coupled with a headwear item, an ocular orbit of a live subject on which the headwear item is disposed, wherein a plurality of ocular stimulator LED packages are coupled with the headwear item, wherein the ocular orbit is a cavity or socket of a skull of the live subject in which an eye of the live subject is situated, and wherein detecting the ocular orbit comprises obtaining geometric data representing a visual focus point associated with the left eye and the right eye of the live subject and determining the ocular orbit based at least in part on the visual focus point of the left eye and the right eye of the live subject; and
  adjusting, using the ocular stimulator circuitry and according to the ocular orbit of the live subject, one or more positions of the plurality of ocular stimulator LED packages, intensities of the plurality of ocular stimulator LED packages, or a schedule associated with light levels provided by the plurality of ocular stimulator LED packages in order to stimulate a pineal gland associated with the live subject.

22. The method of claim 21, wherein the plurality of ocular stimulator LED packages are positioned in front of the ocular orbit of the live subject.

23. The method of claim 21, further comprising stimulating the pineal gland by mimicking, generating, or directing at the live subject a level of light associated with one or more times of day.

24. The method of claim 23, wherein the level of light is one or more of sunrise low-level light associated with an actual or virtual sunrise, daytime full intensity light associated with an actual or virtual day, or sunset low-level light associated with an actual or virtual sunset.

25. The method of claim 23, further comprising receiving, via communication circuitry, instructions for adjusting the level of light associated with one or more times of day.

26. The method of claim 21, further comprising receiving, via communication circuitry, instructions for controlling one or more of the ocular stimulator LED packages from one or more client devices.

* * * * *